(12) United States Patent
Halseth

(10) Patent No.: US 6,969,372 B1
(45) Date of Patent: Nov. 29, 2005

(54) AUTOMATIC RETRACTION HUBER NEEDLE SAFETY ENCLOSURE

(76) Inventor: Thor R. Halseth, 3737 Medea Creek Rd., Agoura Hills, CA (US) 91301

( * ) Notice: Subject to any disclaimer, the term of this patent is extended or adjusted under 35 U.S.C. 154(b) by 237 days.

(21) Appl. No.: 10/338,168

(22) Filed: Jan. 7, 2003

(51) Int. Cl.$^7$ .............................................. A61M 5/178
(52) U.S. Cl. .................. 604/164.08; 128/919
(58) Field of Search ................ 604/93.01, 164.01, 604/164.08, 164.12, 165.01, 165.02, 171, 604/174, 177; 128/DIG. 6, DIG. 26, 917–919

(56) References Cited

U.S. PATENT DOCUMENTS

| | | |
|---|---|---|
| 4,631,058 A | 12/1986 | Raines |
| 4,645,495 A | 2/1987 | Vaillancourt |
| 4,710,176 A | 12/1987 | Quick |
| 5,120,320 A | 6/1992 | Fayngold |
| 5,147,319 A * | 9/1992 | Ishikawa et al. ............. 604/174 |
| 5,395,347 A * | 3/1995 | Blecher et al. ............. 604/198 |
| 5,501,672 A * | 3/1996 | Firth et al. .................... 604/177 |
| 5,562,636 A * | 10/1996 | Utterberg ..................... 604/263 |
| 5,584,813 A | 12/1996 | Livingston et al. |
| 5,704,917 A * | 1/1998 | Utterberg ..................... 604/180 |
| 5,779,679 A * | 7/1998 | Shaw ........................... 604/158 |
| 5,951,522 A | 9/1999 | Rosato et al. |
| 6,500,155 B2 * | 12/2002 | Sasso ............................ 604/177 |
| 6,663,604 B1 * | 12/2003 | Huet ............................. 604/263 |
| 6,676,633 B2 * | 1/2004 | Smith et al. .................. 604/110 |

* cited by examiner

*Primary Examiner*—LoAn H. Thanh
(74) *Attorney, Agent, or Firm*—Jack C. Munro

(57) ABSTRACT

An automatic retraction Huber needle safety enclosure which is designed principally for a Huber needle. A Huber needle is a hypodermic needle that is in the shape of a right angle. The safety enclosure has an internal chamber which is formed between a housing and a lid with the lid being movable relative to the housing between a closed position and an open position. The Huber needle is mounted within the internal chamber. The Huber needle is movable between an extended position and a retracted position. With the Huber needle in the extended position, the Huber needle is capable of being inserted within the body of a human or animal. With the Huber needle in the retracted position, the tip of the Huber needle is to be totally confined within the internal chamber. A wing assembly is attached to the housing which functions to facilitate securement of the safety enclosure to the body of the animal or human and forming an enclosure with the wing assembly folded in abutting juxtaposition.

12 Claims, 5 Drawing Sheets

AUTOMATIC RETRACTION HUBER NEEDLE SAFETY ENCLOSURE

BACKGROUND OF THE INVENTION

1. Field of the Invention

This invention is related to a safety enclosure for a Huber needle in order to keep the Huber needle from inadvertently sticking a medical practitioner during installing and removal of the Huber needle in conjunction with an animal body which includes humans.

2. Description of the Related Art

Within the medical field, more and more patients require the use of vascular access devices as part of their care. Vascular access devices (implanted ports) are used on human patients to supply pain drugs, chemotherapy, antibiotics, anti-viral or anti-fungal drugs as well as for hydration and nutrition. In recent years, there has been a substantial increase in the number of patients with implanted ports. An implanted port requires a special needle to be inserted through the skin of the patient and into the port. The most common type of such a needle includes a ninety degree bend. This type of needle is called a Huber needle. Because of the configuration of the needle, removing of the Huber needle at the end of the infusion therapy is particularly dangerous exposing the medical practitioner to a high degree of risk of inadvertent needlestick injury.

Huber needles are usually designed for longer term infusion therapy. The angular relationship of the needle allows the Huber needle to be more safely anchored to the skin around the port. These needles are commonly left in place for a period of several days, weeks and possibly even months. It is common for the Huber needles to have attached thereto a wing assembly with the wing assembly to be used for securing the Huber needle to the patient by taping the wing members of the wing assembly to the skin of the patient thus facilitating insertion and removal of the Huber needle.

The procedure of removing a Huber needle from an implanted port commonly produces what is called "bounceback" which comprises a rebounding effect. When the needle is mounted in conjunction with the port, the rubber of the port tightly binds about the needle. A substantial force is required when pulling on the needle in order to get it to release from the port. The medical practitioner thus has to pull hard in order to get the needle to release from the port. Once the needle is released, the muscular movement of the medical practitioner then relaxes and an opposite movement takes place, which is called bounceback. Frequently, this bounceback drives the Huber needle point down and can be driven into the medical practitioner's hand or arm. This is called a needlestick injury. The needle is contaminated with the blood of the patient. The patient could have a serious transferable disease, such as AIDS. The medical practitioner could catch the same disease.

There have been prior art types of devices that have been sold for the purpose of decreasing or eliminating needlestick injury. One device consists of a protective member that fits over the port. The medical practitioner then uses a hemostat to pull the needle up in the device for containment during removal of the needle from the patient. The device and the needle is then disposed of. One disadvantage of this technique is that it requires a significant change in the procedure having to do with the removal of the Huber needle and it also requires the use of additional equipment, the hemostat, and it requires a significant amount of dexterity. A second type of device is a scissors type of device formed of two blades which are slid under wings of the needle and against the patient's skin. When the needle is being removed, the bottom blade of the device stabilizes the device while the upper blade pulls out the needle. The needle is held in the blade, but the sharp end remains exposed. This device also requires a significant change in technique in the removing of Huber needles and has a further disadvantage in that it does not fully contain the sharp end of the needle. There is also a device called a Huberlock (trademark). The Huberlock requires a change in technique but it does eliminate pulling a bare needle out of a port. Also, the Huberlock has the disadvantage that it does not fully contain the sharp end of the needle. Also, the Huberlock requires the use of additional equipment which comprises a plastic holder to be used in conjunction with the needle.

Probably the best needle protection device is disclosed within U.S. Pat. No. 5,951,522, entitled Hypodermic Needle Safety Enclosure. This device is not automatically retracting but retracts solely by the application of a manual force. It would be desirable to construct a hypodermic safety needle enclosure which would automatically retract the needle when the needle is pulled from the port eliminating the possibility of bounceback and therefore completely eliminating the possibility of any needlestick injury.

SUMMARY OF THE INVENTION

The first embodiment of automatic retraction Huber needle enclosure utilizes a fixed housing with a wing assembly being mounted on this housing. The wing assembly comprises a pair of wing members that are movable between an extended position where the wing members are in alignment with each other and adapted for mounting onto the body of a human and a collapsed position where the wing members are in a folded position in juxtaposition. A Huber needle is to be mounted within the fixed housing. The Huber needle has a free end with this free end being capable of protruding from the housing. A lid is mounted on the fixed housing with the lid being movable relative to the fixed housing between a lower position and a raised position. With the lid in a lower position there is an internal chamber formed between the lid and the fixed housing, and it is within this internal chamber that the Huber needle is located. A biasing means is to be mounted within the internal chamber and is to connect with the Huber needle. With the lid in a raised position and the wing members in a collapsed position, the Huber needle is to be totally confined within the internal chamber.

A further embodiment of the present invention is where the first basic embodiment is modified by the lid being pivotally mounted relative to the fixed housing.

A further embodiment of the present invention is where the first basic embodiment is modified by the biasing means comprising a coil spring.

A further embodiment of the present invention is where the first basic embodiment is modified by there being included a needle locking mechanism to maintain the Huber needle in a position protruding from the housing.

A further embodiment of the present invention is where the first basic embodiment is modified by there being included a wing locking mechanism that locks the wing members together when in the folded position.

A further embodiment of the present invention is where the first basic embodiment is modified by the lid having a locking slot and the wing members having locking tabs with these locking tabs to engage with the locking slot when the wing members are in the folded position thereby locking the wing members in position.

A second basic embodiment of the present invention comprises an automatic Huber needle safety enclosure which has a housing with a lid being mounted on this housing. An internal chamber is formed between the lid and the housing. A Huber needle is mounted within the internal chamber with the Huber needle having a free end. The Huber needle is movable between an extended position and a retracted position. With the Huber needle in the retracted position, the free end is located within the internal chamber. A wing assembly is mounted on the housing with this wing assembly being movable between a folded position and an expanded position. With the wing assembly in the folded position, the lid connects with the wing assembly.

A further embodiment of the present invention is where the second basic embodiment is modified by there being included a needle locking device to lock the Huber needle in the extended position.

A further embodiment of the present invention is where the second basic embodiment is modified by including a wing assembly locking device that locks the wing assembly to the lid when the wing assembly is in the folded position.

A further embodiment of the present invention is where the second basic embodiment is modified by there being included a biasing means within the internal chamber which is to engage with the Huber needle and is the function to move the Huber needle to totally confine same within the internal chamber when the wing assembly is in the folded position.

A further embodiment of the present invention is where the just previous embodiment is modified by the biasing means comprising a coil spring.

A further embodiment of the present invention is where the second basic embodiment includes a wing locking mechanism to lock the wing assembly when in the folded position.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE INVENTION

Figure 1:
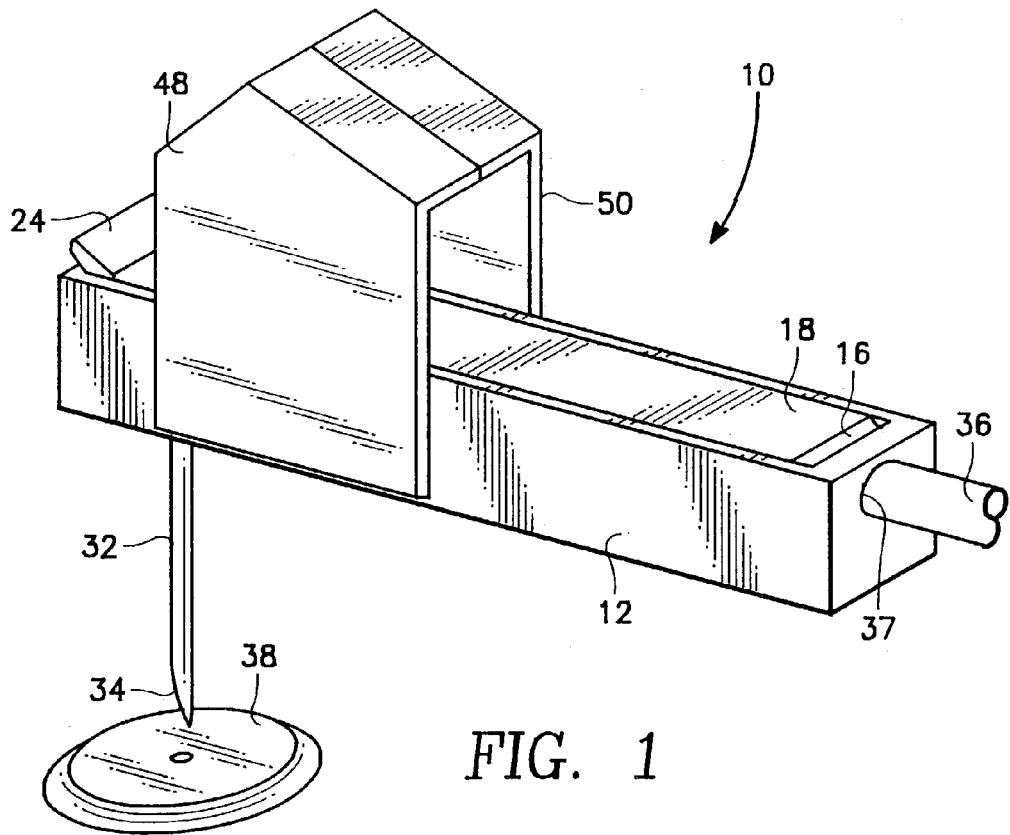
FIG. 1 is an isometric view showing the automatic retraction Huber needle safety enclosure of this invention in a position initiating installation within an implanting port.
Figure 7:
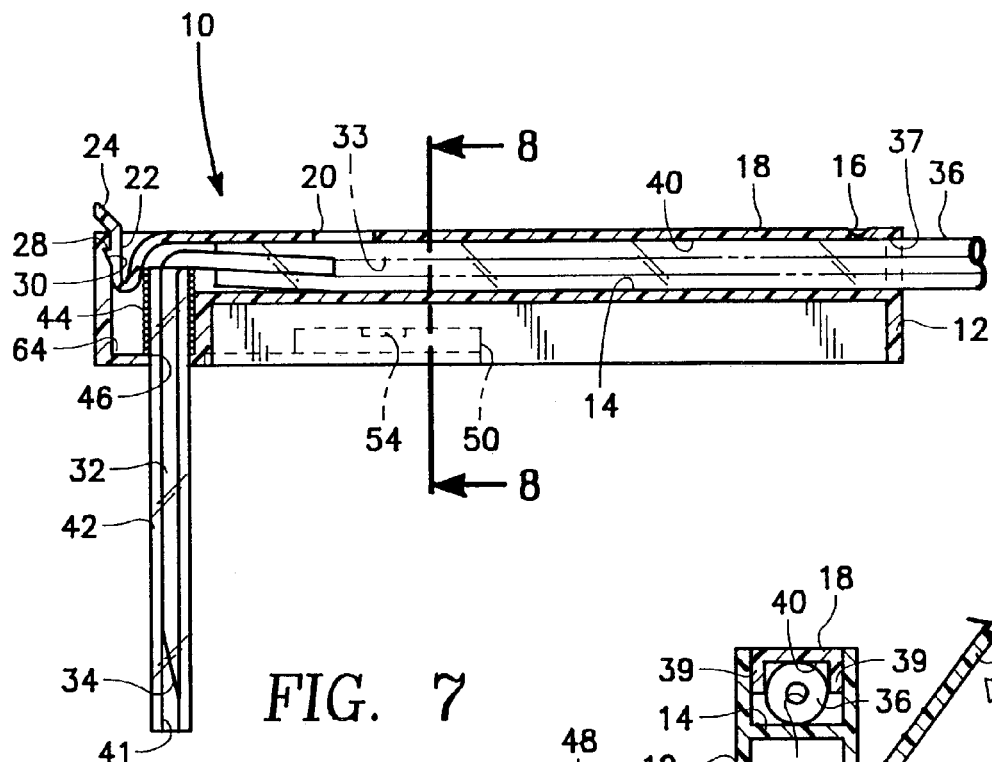
FIG. 7 is a longitudinal cross-sectional view-through the enclosure when in the position of FIG. 1.
Figure 8:
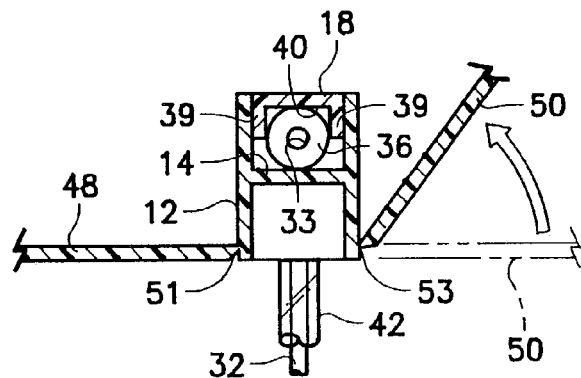
FIG. 8 is a transverse cross-sectional view of the enclosure taken along line 8—8 of FIG. 7.

Referring particularly to the drawings, there is shown the automatic retraction Huber needle enclosure 10 of this invention. The enclosure 10 includes an elongated fixed housing 12. The fixed housing 12 has an internal chamber 14. The fixed housing 12 will normally be constructed of a sheet plastic material. Integrally connected by a living hinge 16 to the aft end of the fixed housing 12 is a lid 18. The lid 18 has formed therein a through slot 20. The slot 20 is located intermediate the ends of the lid 18. The forward end of the lid 18 is formed into a latch 22 which is to lock the Huber needle 32 in the extended position, as is shown in FIGS. 1, 7 and 8. The latch 22 is deflectable by applying of an inward pressure against handle 24 in the direction of arrow 26 in FIG. 4. The application of pressure in the direction of arrow 26 will cause the latch 24 to be deflected sufficiently to disengage protrusion 28 from indentation 30 formed within the fixed housing 12.

The Huber needle 32 is shown in a right angled configuration and has an outer free end formed into a sharpened tip 34. The aft end of the Huber needle 32 is fixedly mounted in a conduit 33 of a plastic tube 36. The tube 36 passes through a hole 37 formed in fixed housing 12. The outer end of the plastic tube 36 is to be connected to a source of liquid (medicine, water, saline, etc.), which is not shown, which is to be supplied through the tube 36 and through the needle 32 to be dispensed into a human body generally by means of an implanted port 38. The implanted port 38 is to be mounted under the skin of the human, which is not shown. It is desired that the tube 36 to be laterally restrained in place. It is for this reason that the lid 18 is formed to have an internal channel 40. The tube 36 will be confined by the sidewalls 39 of the channel 40. The tube 36 may actually be connected by some kind of a connecting clip mounted in conjunction with the lid 18 thereby fixing in position the tube 36 relative to the lid 18. However, the use of any type of securement, such as a clip, will normally not be necessary.

Prior to installation of the Huber needle 32 within the port 38, there is mounted about the needle 32 a protective sleeve 42 with needle 32 being snugly held in passage 41 of sleeve 42. This protective sleeve 42 will extend exteriorly of the sharpened tip 34. It is the function of the protective sleeve 42 to keep a medical practitioner from incurring a needle-stick injury due to being inadvertently stuck with the sharpened tip 34 prior to installation of the sharpened tip 34 within the port 38 as the sleeve 42 extends beyond sharpened tip 34 of the needle 32 preventing any penetration of tip 34 in an exterior object. The port 38 will generally comprise a rubber or rubberized plastic material. The sharpened tip 34 can readily penetrate the port 38 to gain access to a vascular vein or artery located within the body of a human. Surrounding the protective sleeve 42 is a coil spring 44. The coil spring 44 is compressed between the wall of the internal chamber 14 of the fixed housing 12 and the interior wall surface of the lid 18 when the lid 18 is in the closed position with the protrusion 28 located within indentation 30. The protective sleeve 42 also functions as a guide for the coil spring 44 to keep the coil spring 44 aligned and not waffling sideways as it is compressed. The sharpened tip 34, the protective sleeve 42 and the outer end of the Huber needle 32 all protrude through hole 46 formed in the fixed housing 12.

Figure 2:
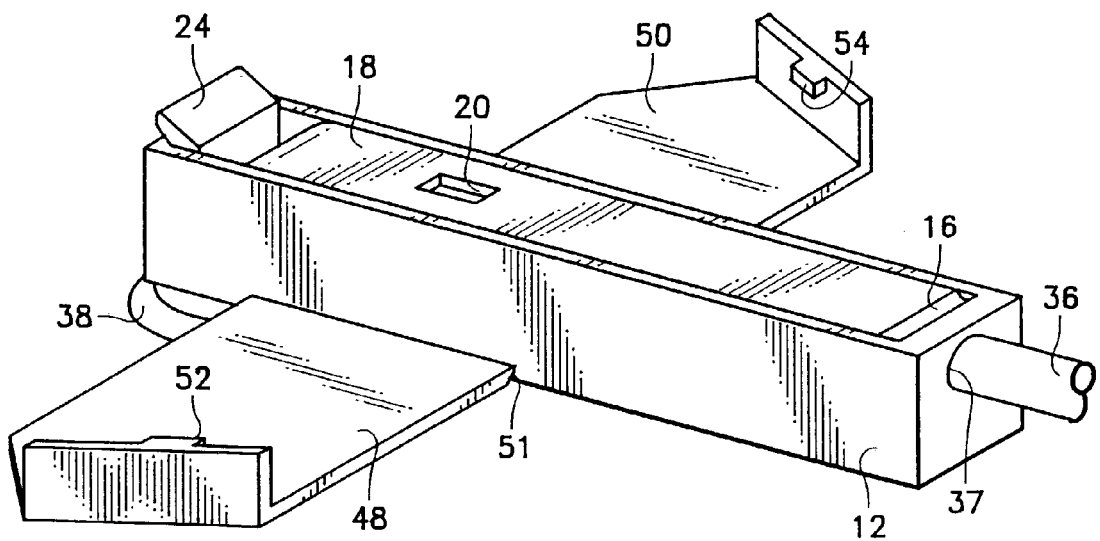
FIG. 2 is an isometric view showing the position of the enclosure immediately after installation within the port with the wing assembly of the enclosure expanded.

Pivotally mounted by a living hinge 51 to the fixed housing 12 is a left wing 48 and by living hinge 53 is a right wing 50 of a wing assembly. The left wing 48 and the right wing 50 can be mounted in an aligned position, which is also the open position of the wing assembly. This aligned position is clearly shown in FIG. 2. The left wing 48 and right wing 50 can each be folded about ninety degrees to be in juxtaposition with each other, which is called the folded position and which is clearly shown in FIGS. 1, 4 and 5 of the drawings. The internal surface of the left wing 48 includes a tab 52. The internal surface of the right wing 50 also includes a similar tab 54.

The operation of the enclosure shown in FIGS. 1–8 of the drawings is as follows: The medical practitioner will receive the enclosure 10 after being removed from its package in either the position of FIG. 1 or FIG. 2. If the enclosure 10 is in the position of FIG. 2, the medical practitioner will immediately fold the left wing 48 and the right wing 50 to the folded position, as shown in FIG. 1. The medical practitioner will then grab the wing assembly composed of left wing 48 and right wing 50. The medical practitioner will place a finger directly onto the handle 24. The medical practitioner will then grab protective sleeve 42 and slide such from the Huber needle 32 removing same. The medical practitioner will then proceed to insert sharpened tip 34 into the port 38 and push such sufficiently hard to penetrate the desired distance. To facilitate this penetration, manual force is applied from the medical practitioner's finger through handle 24 which will result in force being applied directly to the needle 32 for it to be forcibly inserted the proper distance.

Figure 3:
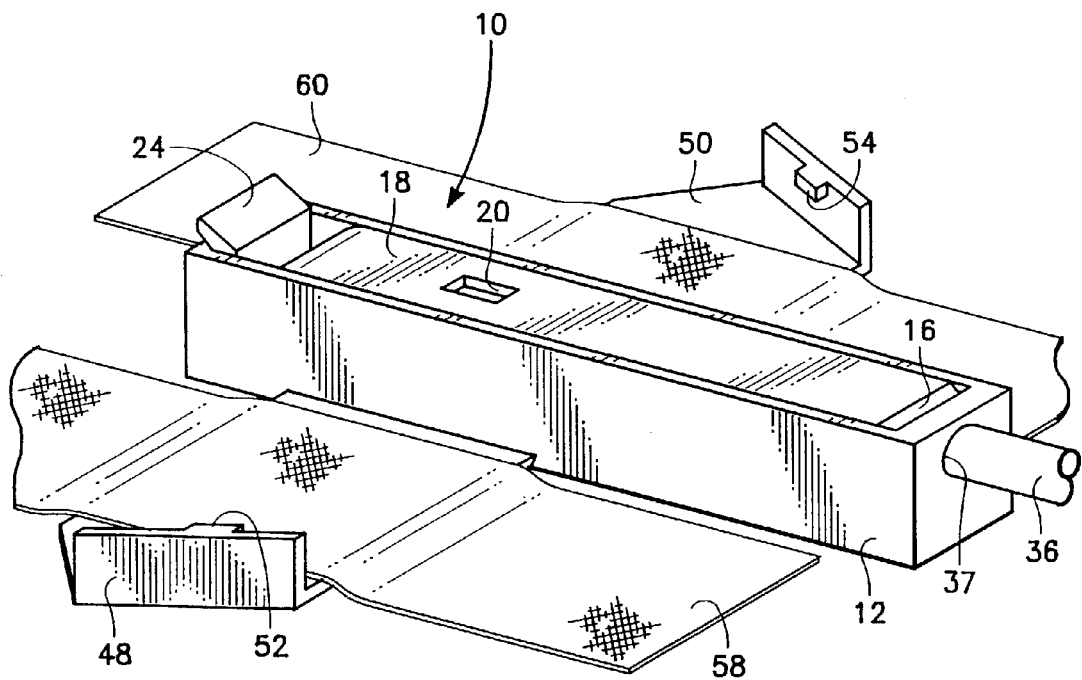
FIG. 3 is an isometric view similar to FIG. 2 showing the application of adhesive strips to the wing assembly to secure in position the enclosure on the body of the patient.

At the time the Huber needle 32 is properly inserted, the medical practitioner then unfolds the wing assembly to place left wing 48 and right wing 50 in alignment with each other and in direct contact against the patient's skin. The medical practitioner will then take an adhesive strip 58 and place it over the wing 48 and against the patient's skin (FIG. 3). The medical practitioner will then take an adhesive strip 60 and place such over the wing 50 and cause such to adhere to the patient's skin (FIG. 3). The Huber needle 32 and the enclosure 10 are now properly installed.

Figure 4:
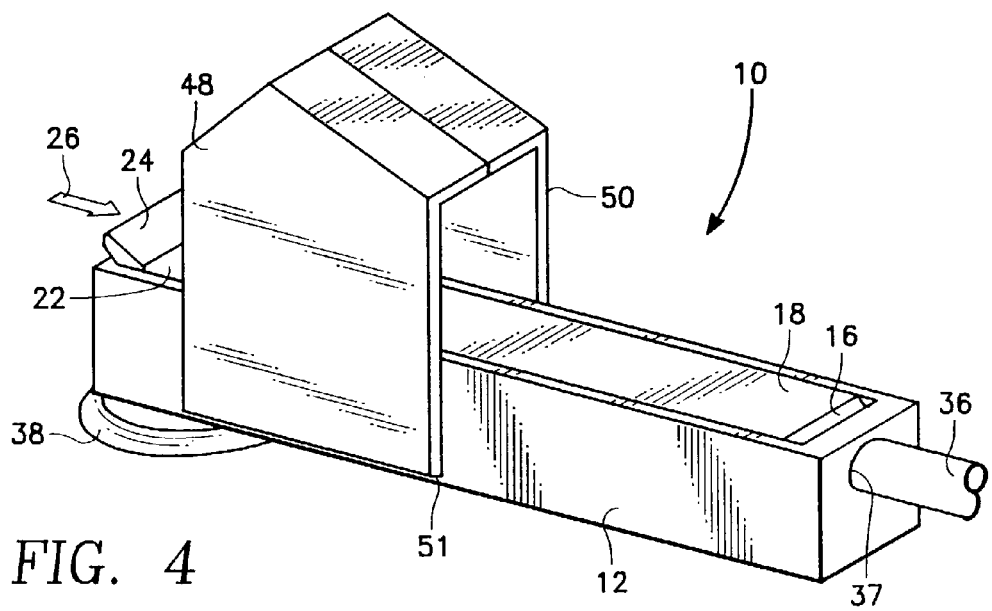
FIG. 4 is an isometric view showing the adhesive strips removed and the wing assembly moved to a folded position positioning the enclosure for removal from the implanted port.
Figure 5:
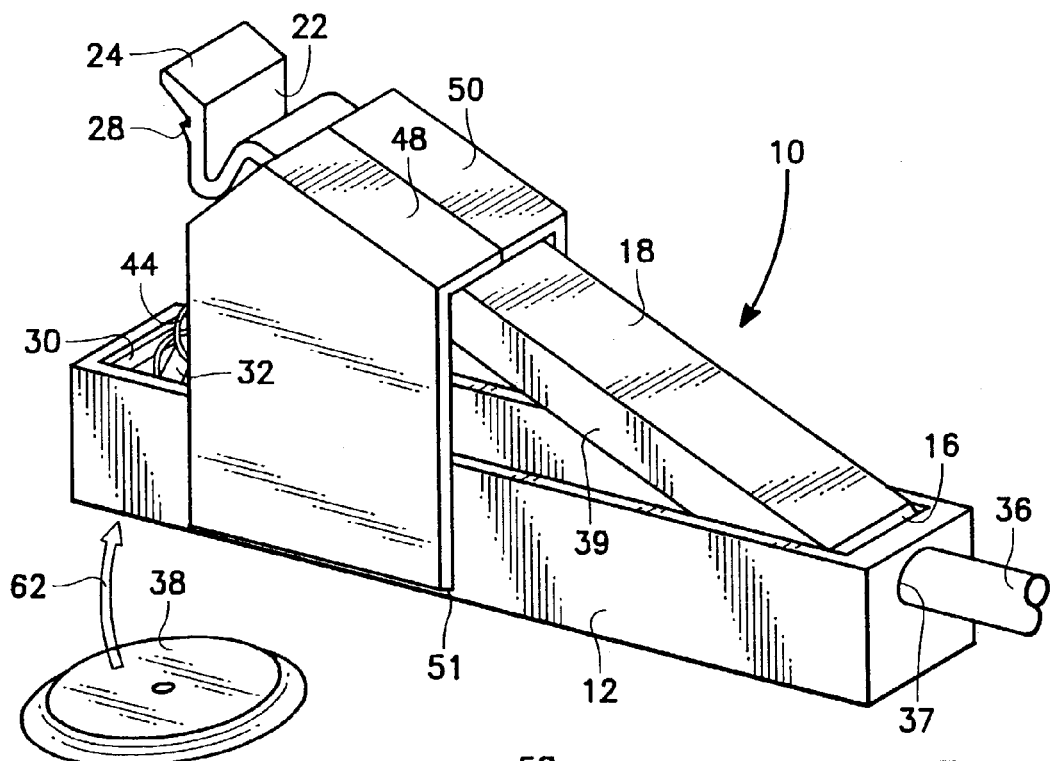
FIG. 5 is an isometric view showing the enclosure just having been removed from the implanted port.
Figure 6:
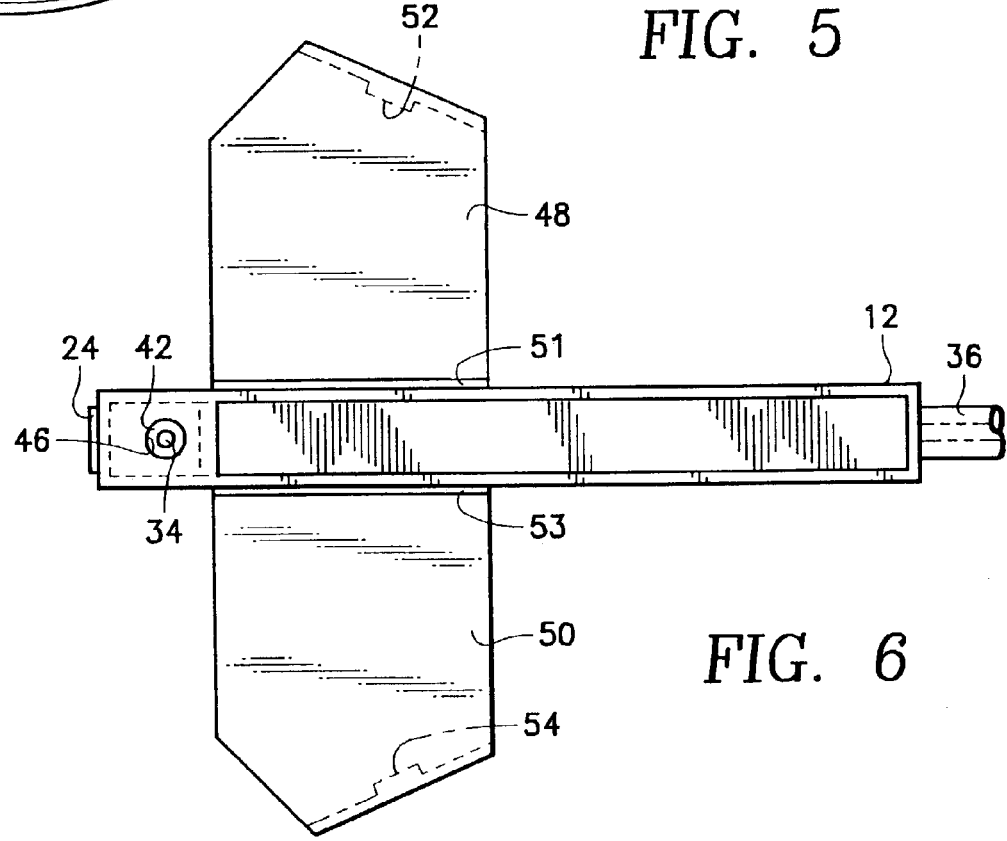
FIG. 6 is a bottom plan view of the enclosure when in the position of FIG. 2.
Figure 9:
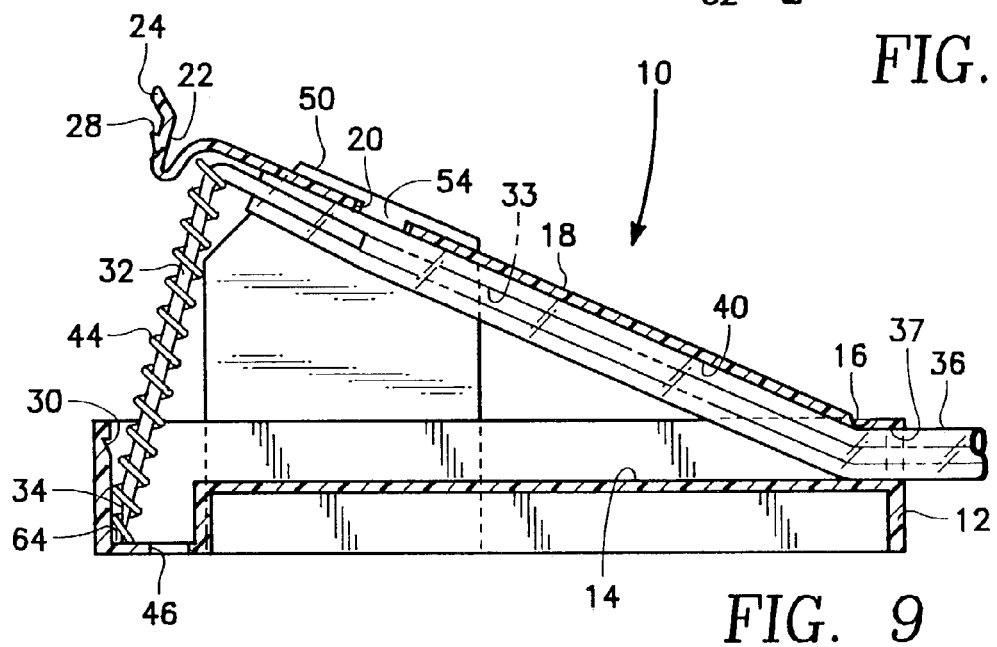
FIG. 9 is a longitudinal cross-sectional view of the enclosure when in the position of FIG. 5.

Let is now be assumed that it is necessary to remove the Huber needle 32 and the enclosure 10 from its installed position. The medical practitioner will first remove adhesive strips 58 and 60 and discard such. The medical practitioner will then fold the wing assembly composed of left wing 48 and right wing 50 to the folded position, which is shown in FIG. 4. The medical practitioner will then apply a pressure inwardly shown by arrow 26 against the handle 24 to disengage the protrusion 28 from the indentation 30. This will mean that the lid 18 will be capable of being moved relative to the fixed housing 12. However, there is a sufficient resistance caused by the port 38 on the Huber needle 32 which will prevent this movement. The medical practitioner will then exert an upward force in the direction of arrow 62 in FIG. 5 until the Huber needle disengages from the port 38. At the instant of that disengagement, and there is no more resistance being applied to the needle 32 by the port 38, the coil spring 44 will immediately expand and cause the lid 18 to move to the upper position, shown in FIGS. 5 and 9. The tabs 52 and 54 will enter the slot 20 preventing the left wing 48 and the right wing 50 from moving from the folded position to the unfolded position, shown in FIGS. 2 and 6. The needle 32 is confined within the internal chamber 14 with the internal chamber 14 being defined as the total space between the fixed housing 12 in the lid 18. The sharpened tip 34 will now be located at corner 64 of the fixed housing 12. This means that the sharpened tip 34 is confined, does not extend exteriorly of the fixed housing 12 and is not capable of causing any needlestick injury. At this particular time, the entire enclosure, which includes the needle 32, is then to be appropriately disposed of.

Figure 10:
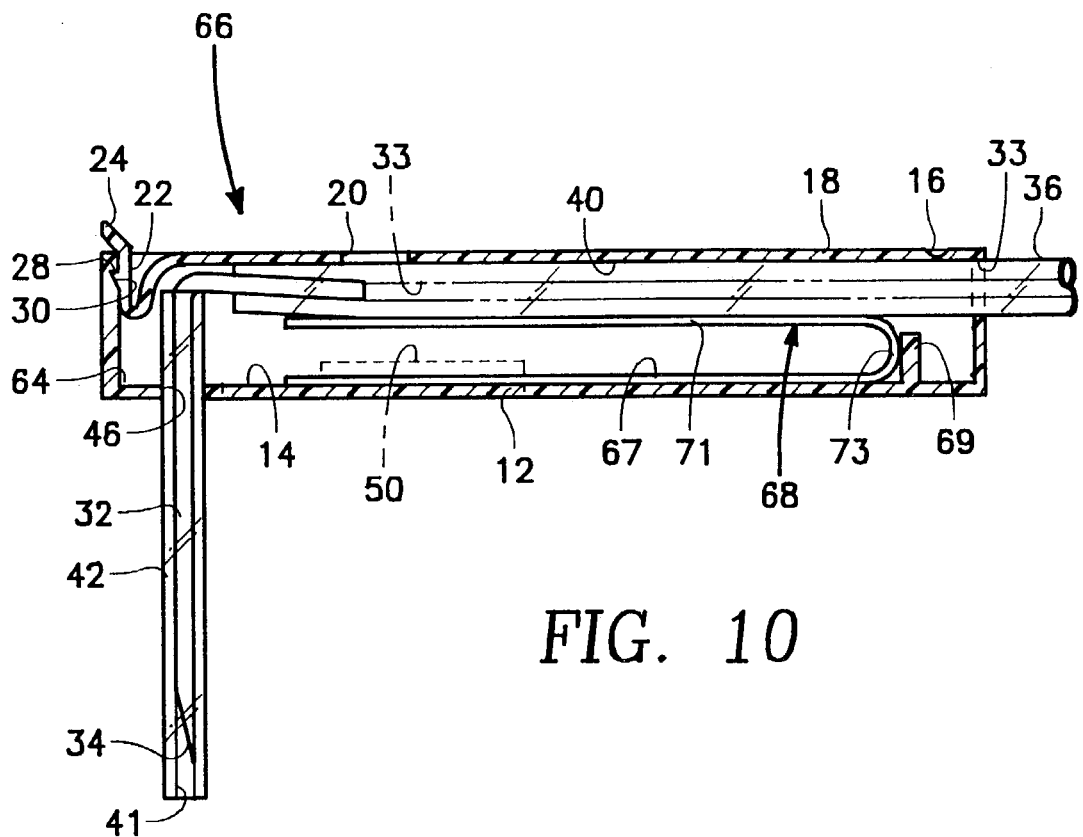
FIG. 10 is a longitudinal cross-sectional view similar to FIG. 7 but instead of using a coil spring, as shown in FIG. 7, there is utilized a leaf spring.
Figure 11:
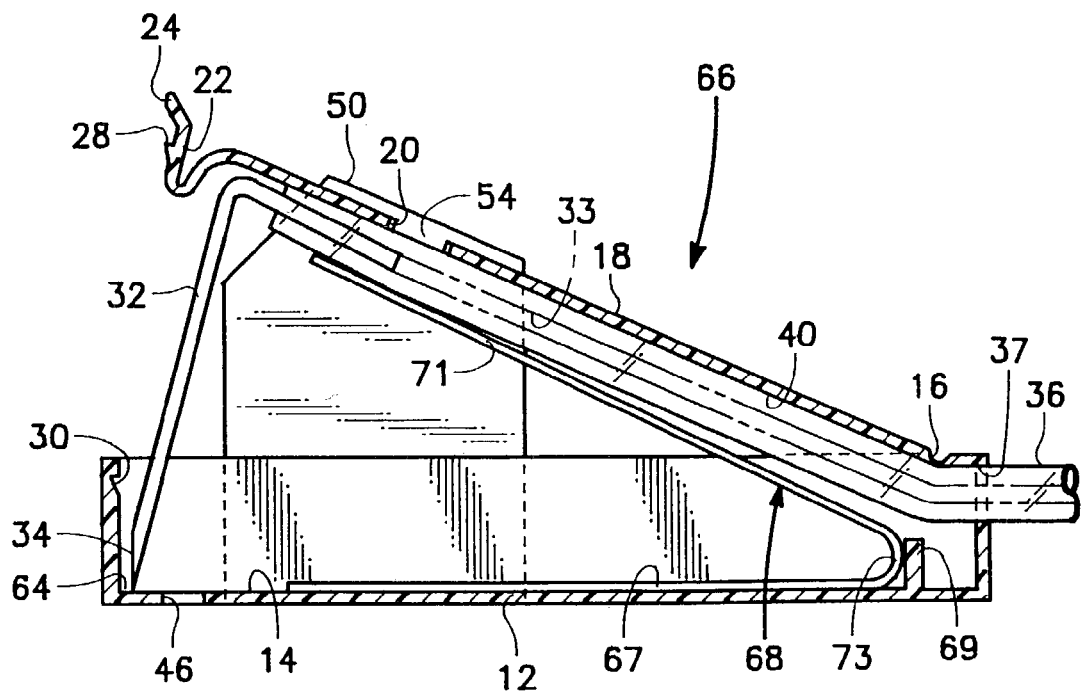
FIG. 11 is a view similar to FIG. 8 but of the leaf spring structure of FIG. 9.

Referring to FIGS. 10 and 11, there is shown a second embodiment 66 of enclosure of this invention. Like numerals have been utilized to refer to like parts. The only real difference of the second embodiment 66 relative to the first embodiment 10 of the enclosure of this invention is that the coil spring 44 is eliminated and instead there is utilized a leaf spring 68. The leaf spring 68 is in the shape of a hairpin with one leg 67 of the leaf spring 68 to be in continuous contact with the fixed housing 12 and the opposite leg 71 of the leaf spring 68 to be in contact with the tube 36. The apex 73 of the leaf spring 68 abuts against a stop 69 mounted on the fixed housing 12 and located within internal chamber 14. The leaf spring 68 will function in the same manner as the coil spring 44 to cause the enclosure 10 to move from the closed position, shown in FIG. 10, to the expanded position of FIG. 11 when the second embodiment 66 of enclosure is moved upwardly disengaging the needle 32 from the port 38.

What is claimed is:

1. An automatic retraction Huber needle enclosure when said Huber needle has a free end that is formed into a sharpened tip comprising:
    a fixed housing;
    a wing assembly mounted on said fixed housing, said wing assembly comprising a pair of wing members that are movable between an extended position where said wing members are in alignment with each other adapted for mounting onto an animal body and a collapsed position where said wing members are in a folded position in juxtaposition;
    a Huber needle mounted within said fixed housing, said Huber needle having a free end, said free end capable of protruding from said housing;
    a lid mounted on said fixed housing, said lid being movable relative to said fixed housing between a lower position and a raised position, with said lid in said lower position there being an internal chamber formed between said lid and said fixed housing, a portion of said Huber needle being located within said internal chamber; and
    a biasing means mounted within said internal chamber and connecting with said Huber needle, with said lid in said raised position, and said wing members in said collapsed position said sharpened tip of said Huber needle is to be totally confined within said internal chamber.

2. The automatic retraction Huber needle enclosure as defined in claim 1 wherein:
    said lid being pivotally mounted on said fixed housing.

3. The automatic retraction Huber needle enclosure as defined in claim 1 wherein:
    said biasing means comprising a coil spring.

4. The automatic retraction Huber needle enclosure as defined in claim 1 wherein:
    a needle locking mechanism to maintain said Huber needle in a position protruding from said housing.

5. The automatic retraction Huber needle enclosure as defined in claim 1 wherein:

a wing locking mechanism that locks said wing members together when in said folded position.

6. The automatic retraction Huber needle enclosure as defined in claim 1 wherein:

said lid having a locking slot, said wing members having locking tabs, said locking tabs engaging with said locking slot when said wing members are in juxtaposition thereby locking said wing members in position.

7. The automatic retraction Huber needle enclosure as defined in claim 1 wherein:

said biasing means comprising a leaf spring.

8. An automatic retraction Huber needle safety enclosure comprising:

a housing;

a lid mounted on said housing;

an internal chamber formed between said lid and said housing;

a Huber needle mounted within said internal chamber, said Huber needle having a free end, said Huber needle being movable between an extended position and a retracted position, with said Huber needle in said retracted position said free end being located within said internal chamber;

a wing assembly mounted on said housing, said wing assembly being movable between a folded position and an expanded position, with said wing assembly in said folded position said lid connecting with said wing assembly; and a needle locking device to lock said Huber needle in said extended position.

9. An automatic retraction Huber needle safety enclosure comprising:

a housing;

a lid mounted on said housing;

an internal chamber formed between said lid and said housing;

a Huber needle mounted within said internal chamber, said Huber needle having a free end, said Huber needle being movable between an extended position and a retracted position, with said Huber needle in said retracted position said free end being located within said internal chamber;

a wing assembly mounted on said housing, said wing assembly being movable between a folded position and an expanded position, with said wing assembly in said folded position said lid connecting with said wing assembly; and a wing assembly locking device that locks said wing assembly to said lid when said wing assembly is in said folded position.

10. An automatic retraction Huber needle safety enclosure comprising:

a housing;

a lid mounted on said housing;

an internal chamber formed between said lid and said housing;

a Huber needle mounted within said internal chamber, said Huber needle having a free end, said Huber needle being movable between an extended position and a retracted position, with said Huber needle in said retracted position said free end being located within said internal chamber;

a wing assembly mounted on said housing, said wing assembly being movable between a folded position and an expanded position, with said wing assembly in said folded position said lid connecting with said wing assembly;

said lid being pivotally movable between a closed position and an open position; and a biasing means mounted between said lid and said housing, said biasing means being located within said internal chamber, said biasing means engaging with said Huber needle, said biasing means functioning to force said Huber needle against said lid when said lid is in said open position.

11. The automatic retraction Huber needle safety enclosure as defined in claim 10 wherein:

said biasing means comprising a coil spring.

12. The automatic retraction Huber needle safety enclosure as defined in claim 10 wherein:

said biasing means comprising a leaf spring.

* * * * *